United States Patent

Mingasson et al.

[11] 4,017,506
[45] Apr. 12, 1977

[54] PROCESS FOR THE PREPARATION OF 2-BENZO THIAZOLE SULPHINAMIDES

[75] Inventors: Georges Raymond Henry Mingasson, Paris; Michel Louis Jules Montu, Enghien les Bains; Michel Jean Camille Alicot, Soisy sous Montmorency, all of France

[73] Assignee: Ugine Kuhlmann, Paris, France

[22] Filed: Jan. 27, 1975

[21] Appl. No.: 544,540

Related U.S. Application Data

[63] Continuation-in-part of Ser. No. 862,920, Oct. 1, 1969, abandoned.

[30] Foreign Application Priority Data

Oct. 2, 1968   France ............................ 68.168410
Apr. 30, 1969  France ............................. 69.13809

[52] U.S. Cl. ............... 260/306.6 R; 260/247.1 L; 260/293.57
[51] Int. Cl.² ..................................... C07D 277/80
[58] Field of Search ............... 260/306.6 R, 293.57, 260/247.1

[56] References Cited

UNITED STATES PATENTS 2,957,002  10/1960  Korman ................... 260/293.57 X
3,454,590   7/1969  Meale et al. .................... 260/306.6

Primary Examiner—Nicholas S. Rizzo
Assistant Examiner—David B. Springer
Attorney, Agent, or Firm—Beveridge, DeGrandi, Kline & Lunsford

[57] ABSTRACT

A process for the preparation of 2-benzothiazolesulphinamides of the general formula:

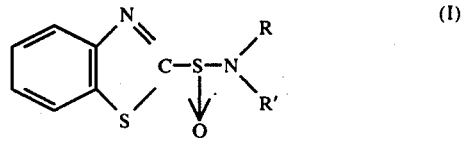

in which R and R' represent alkyl groups containing 1 to 6 carbon atoms, cyanoethyl or cycloalkyl groups containing 5 to 7 carbon atoms or -NRR' is piperidino, hexamethyleneimino, morpholino, or 2,6-dimethylmorpholino which comprises oxidizing with an alkali metal hypochlorite, at a temperature below 30° C. an aqueous suspension of a sulphenamide of the formula:

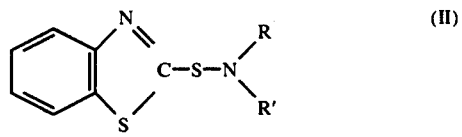

in which R and R' have the same significance as in formula (I) in the presence of a sufficient amount of an alkaline agent selected from sodium carbonate, sodium bicarbonate, potassium carbonate, potassium bicarbonate and mixtures thereof so as to maintain the pH at 9 to 10, and as novel compounds useful as vulcanization accelerators for natural or synthetic rubber 2-piperidino-sulphinyl-, 2-N,N-bis(-β-cyanoethyl)aminosulphinyl-, 2',6'-dimethyl-2-morpholinosulphinyl- and 2-N-hexamethyleneiminosulphinyl-benzothiazoles.

6 Claims, No Drawings

PROCESS FOR THE PREPARATION OF 2-BENZO THIAZOLE SULPHINAMIDES

The present application is a continuation-in-part application of our copending application Ser. No. 862,920 filed on Oct. 1, 1969, now abandoned. The entire disclosure of this co-pending application is relied upon and incorporated herein by reference.

The present invention relates to a new process for the preparation of 2-benzothiazole-sulphinamides corresponding to the general formula:

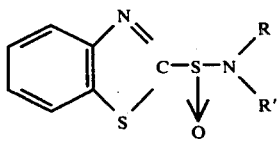
(I)

in which R and R' represent alkyl containing 1 to 6 carbon atoms, cyanoethyl or cycloalkyl groups containing 5 to 7 carbon atoms or —NRR' is piperidino, hexamethyleneimino, morpholino or 2,6-dimethylmorpholino which comprises oxidising by an alkali metal hypochlorite, preferably sodium hypochlorite, and at a temperature below 30° C. an aqueous suspension of a sulphenamide of the formula:

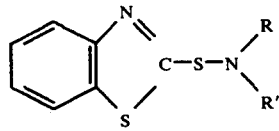
(II)

in which R and R' have the same significance as in formula (I) in the presence of a sufficient amount of an alkaline agent selected from the group consisting of sodium carbonate, potassium carbonate, sodium bicarbonate, potassium bicarbonate and mixtures thereof so as to maintain the pH at 9 to 10.

The invention also includes 2-piperidinosulphinyl-, 2-N,N-bis (β-cyanoethyl) aminosulphinyl-, 2',6'-dimethyl-2-morpholinosulphinyl- and 2-N-hexamethylene-iminosulphinyl-benzothiazoles which are novel products and may be used as vulcanization accelerators for natural or synthetic rubbers.

In French Pat. No. 1,003,821 a method of preparation of the dimethylamide of 2-benzo-thiazolesulphinic acid of the formula:

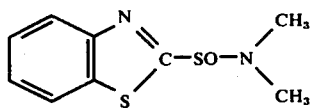

has been described, which comprises oxidising an aqueous solution of mercaptobenzothiazole or benzothiazyl disulphide in a large excess of dimethylamine, this excess being necessary in order to keep in solution the intermediate sulphenamide formed. The oxidising agent used is sodium chlorite or hypochlorite, or hydrogen peroxide. This process has two drawbacks: that of requiring a large excess of amine which must be recovered, and also of having to keep the intermediate oxidation product in solution, which favours a further oxidation of the latter into sulphonic acid resulting in a loss of yield.

In French Pat. No. 1,529,050 a method is described very like the preparation of compounds of the formula:

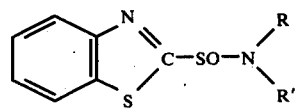

which comprises oxidising with sodium hypochlorite the corresponding sulphenamide in a solvent miscible with water, at a temperature between 30° C. and 80° C. the boiling point of the solvent, for example methanol, being even considered as advantageous. The published yields are small.

We have now found that benzothiazole sulphenamide can advantageously be oxidised to sulphinamide with a high yield of a product of good purity by oxidising at a temperature below 30° C. by an alkali metal hypochlorite, preferably by sodium hypochlorite, an aqueous suspension of the sulphenamide. The oxidation must be carried out in the presence of an alkaline agent, selected from sodium carbonate, sodium bicarbonate, potassium carbonate, potassium bicarbonate and mixtures thereof so as to maintain the pH at 9 to 10. No sulphinamide is obtained in the absence of the alkaline agent.

The starting materials used to carry out the process of the present invention have the general formula:

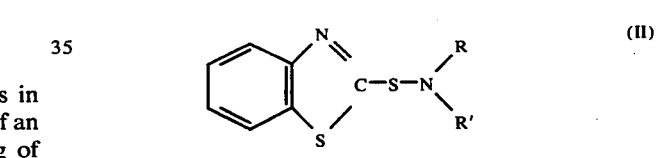
(II)

in which R and R' have the same significance as in the formula (I). The alkyl groups represented by R or R' may have straight or branched chains. These sulphenamides may be prepared for example by any known process; in particular, they may be obtained by oxidation with sodium hypochlorite of an aqueous solution of a 2-mercapto-benzothiazole salt with an amine of the formula $$NH\begin{matrix}R\\R'\end{matrix}$$

wherein R and R' have the meanings given in formula (I).

The invention is illustrated by, but not limited to, the following Examples in which the parts given are parts by weight.

EXAMPLE 1

2-N,N-dimethylbenzothiazole-sulphinamide or 2-N,N-dimethylsulphinamoyl-benzothiazole 10 parts of sodium carbonate and 4 parts of sodium bicarbonate are added to a well stirred suspension of 63 parts 2-N,N-dimethylbenzothiazole-sulphenamide in 130 parts of water. 170 parts by volume of a solution of sodium hypochlorite titrating 177 g. of NaClO and 3 g. of free caustic soda per liter are then slowly introduced, in about 5 hours and keeping the temperature within the range from 25° C. to below 30° C. The excess of hypochlorite is controlled by starchiodide paper. After introduction, the mixture is stirred for a further hour. The creamy white precipitate obtained is filtered off, washed until the washings are neutral and dried at 60° C. The 2-N,N-dimethyl-benzothiazole-sulphinamide melting at 121°–122° C., free from dibenzothiazyl disulphide, is obtained with a yield of 90%.

The 2-N,N-dimethylbenzothiazole-sulphenamide used in this Example can be obtained as follows: 5.5 parts of anhydrous dimethylamine are introduced into a stirred mixture of 7 parts of water and 12 parts of crushed ice, with exterior cooling so that the temperature does not exceed 15° C. 20 parts of mercaptobenzothiazole are gradually added while the temperature is maintained below 30° C. When solution is complete, a solution of sodium hypochlorite titrating 170 g. of NaClO per liter is introduced in a period of 5 hours at a constant rate until the mercaptobenzothiazole disappears. The temperature is maintained at between 30° C. and 35° C. during the whole addition of hypochlorite. The sulphenamide separates in a pasty form. The reaction mass is cooled to 15° C. and diluted with vigorous stirring with 80 parts of ice water. The sulphenamide separates as small hard granules with a melting point of 35° C. It is washed several times in cold water by decantation until the washings are neutral. The sulphenamide is then ready for use for its conversion into sulphinamide.

EXAMPLE 2

2-Morpholinosulphinyl-benzothiazole 37.8 parts of 2-morpholinosulphenyl-benzothiazole are suspended in 65 parts of water containing 5 parts of sodium carbonate and 1 part of sodium bicarbonate. 90 parts by volume of an aqueous solution of sodium hypochlorite titrating 177 g. of NaClO and 3 g. of free caustic soda per liter are slowly introduced in a period of one hour into the well stirred suspension. The temperature is maintained at 25° C. and the mixture is stirred for 20 hours at this temperature. It is filtered, the solid is washed until neutral and dried under vacuum. 37 parts of 2-morpholinosulphinyl-benzothiazole melting at 93°–94° C. are obtained, that is a yield of 93%. On recrystallisation from a benzene/petrol ether mixture, the melting point is 99° C. (uncorrected).

EXAMPLE 3

2-Piperidinosulphinyl-benzothiazole 125 parts of 2-piperidinosulphenyl-benzothiazole suspended in 625 parts of water are introduced into an apparatus fitted with a stirrer and a thermometer. 20 parts of sodium carbonate and 12 parts of sodium bicarbonate are added. The mixture is cooled to a temperature between −5° C. and 0° C. and 400 parts by volume of a sodium hypochlorite solution titrating 180 g. per liter of NaClO are gradually added in a period of 2 hours with good stirring. During the introduction of the sodium hypochlorite, the temperature is maintained at between −2° C. and −3° C. It is then allowed to rise and stirring is continued for a further 15 hours at the ambient temperature. The solid is filtered off, washed with water until neutral and dried in vacuo.

109 parts of 2-piperidinosulphinyl-benzothiazole are obtained, that is a yield of 82%. This new compound has a melting point (uncorrected) of 86.5° C. On recrystallising from hexane, a product of melting point (uncorrected) of 88° C. is obtained.

Analysis ($C_{12}H_{14}N_2S_2O$) Calculated: C%, 54.10; H%, 5.27; N%, 10.54; S%, 24.04. Found: C, 53.85; H, 5.26; N, 10.18; S, 24.26.

EXAMPLE 4

2-N,N-diisopropylaminosulphinyl-benzothiazole 133 parts of N,N-diisopropyl-2-benzothiazolesulphenamide are suspended in 400 parts of water in an apparatus provided with a stirrer and a thermometer. 20 parts of sodium carbonate and 20 parts of sodium bicarbonate are added. 400 parts by volume of a sodium hypochlorite solution titrating 180 g. per liter of NaClO are gradually introduced in a period of 1 hour, with good stirring, at a temperature of 25°–28° C. The mixture is stirred for a further 10 hours at 20°–25° C. The solid is filtered off, washed with water until neutral and dried in vacuo. 119 parts of 2-N,N-diisopropylbenzo-thiazole-sulphinamide are obtained, that is a yield of 84.5%. Melting point (uncorrected): 79.5° C. After recrystallising from ethyl alcohol, a product of melting point (uncorrected) 80.5° C. is obtained.

Analysis ($C_{13}H_{18}N_2S_2O$)

Calculated: C%, 55.40; H%, 6.38; N%, 9.92; S%, 22.70.

Found: C, 55.35; H, 6.18; N, 10.16; S 22.12.

EXAMPLE 5

2-N,N-bis(β-cyano-ethyl)-aminosulphinyl-benzothiazole 144 parts of N,N-bis(β-cyanoethyl)-2-benzothiazolesulphenamide are suspended in 400 parts of water in an apparatus similar to that previously mentioned. 20 parts of sodium carbonate and 20 parts of sodium bicarbonate are added and 400 parts by volume of a sodium hypochloride solution titrating 178 g. per liter of NaClO are introduced in a period of 2½ hours with good stirring.

The reaction is slightly exothermic. The temperature is maintained at 25°–28° C. and the mixture is stirred for 15 hours at this temperature. The solid is filtered off, washed with water until neutral and dried in vacuo.

145 parts of 2-N,N-bis(β-cyanoethyl)aminosulphinylbenzothiazole are obtained, that is a yield of 95.5%. This new product has a melting point (uncorrected) of 143° C. After recrystallising from an ethyl alcohol-dioxan mixture containing 40% by volume of dioxan, a compound of melting point (uncorrected) 147° C. is obtained.

Analysis ($C_{13}H_{12}N_4S_2O$)

Calculated: C%, 51.30; H%, 3.95; N%, 18.42; S%, 21.

Found: C, 51.47; H, 4.18; N, 18.11; S, 20.59.

EXAMPLE 6

2',6'-dimethyl-2-morpholinosulphinyl-benzothiazole 70 parts of 2',6'-dimethyl-2-morpholino-sulphenyl-benzothiazole are suspended in 250 parts of water in an apparatus similar to those previously mentioned. 10 parts of sodium carbonate and 7 parts of sodium bicarbonate are added. 200 parts of a solution of sodium hypochlorite titrating 180 g. per liter of NaClO are introduced in 2 hours at 25° C. with good stirring. The mixture is stirred for a further 12 hours, always at a temperature of 25° C., and the solid is filtered off, washed with water until neutral and dried in vacuo.

65 parts of 2',6'-dimethyl-2-morpholino-sulphinyl-benzothiazole are obtained, that is a yield of 88%. This new product has a melting point (uncorrected) of 110° C. On recrystallising from hexane a product with melting point (uncorrected) of 113° C. is obtained.

Analysis ($C_{13}H_{16}N_2S_2O_2$)

Calculated: C%, 52.70; H%, 5.40; N%, 9.46; S%, 21.62.

Found: C, 52.56; H, 5.27; N, 9.18; S, 21.28.

EXAMPLE 7

2-N,N-dicyclohexylaminosulphinyl-benzothiazole 173 parts of N,N-dicyclohexyl-2-benzothiazolesulphenamide are suspended in 400 parts of water in an apparatus similar to those previously mentioned. 20 parts of sodium carbonate and 20 parts of sodium bicarbonate are added. 700 parts by volume of a solution of sodium hypochlorite titrating 160 g. per liter of NaClO are introduced at 20°-25° C. in an hour, with good stirring. The mixture is stirred at the same temperature for 15 hours. It is then filtered under vacuum, the solid is washed with water until neutral and dried in vacuo. 167 parts of N,N-dicyclohexyl-2-aminosulphinyl-benzothiazole are obtained, that is a yield of 92.3%, with a melting point (uncorrected) of 127° C. On recrystallising from a mixture of hexane and ethyl alcohol (50—50 by volume) a product with a melting point (uncorrected) of 132° C. is obtained.

Analysis ($C_{19}H_{26}N_2S_2O$)

Calculated: C%, 63.00; H%, 7.18; N%, 7.73; S%, 17.70.

Found: C, 63.40; H, 7.40; N, 7.19; S, 17.51.

EXAMPLE 8

2-N-hexamethylene-iminosulphinyl-benzothiazole 132 parts of 2-N-hexamethylene-iminosulphenyl-benzothiazole are suspended in 400 parts of water containing 2 parts of sodium dibutylnaphthalene-sulphonate. 20 parts of sodium carbonate and 20 parts of sodium bicarbonate are added. 760 parts by volume of a solution of sodium hypochlorite titrating 150 g. per liter of NaClO are added in about an hour, with brisk stirring. Since the oxidation reaction is exothermic, cooling is effected during the introduction of the oxidising agent so that the temperature does not exceed 25° C. The mixture is then cooled to between 5° C. and 10° C. and stirred at this temperature for 12 hours. The solid is filtered off, washed with water until neutral and dried in vacuo. 124 parts of 2-N-hexamethylene-iminosulphinyl-benzo-thiazole, that is a yield of 88.5% are thus obtained. This new compound has a melting point (uncorrected) of 53° C. On recrystallising from an ethyl alcohol-water mixture, a melting point of 56°-57° C. is obtained.

Analysis ($C_{13}H_{16}N_2S_2O$)

Calculated: C%, 55.70; H%, 5.72; N%, 10.00; S%, 22.84.

Found: C, 55.64; H, 5.78; N, 10.46; S, 22.67.

We claim:

1. A process for the preparation of 2-benzothiazolesulphinamides of the formula:

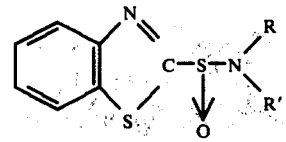

in which R and R' represent alkyl groups containing from 1 to 6 carbon atoms, cyanoethyl or cycloalkyl groups containing from 5 to 7 carbon atoms or —NRR' is piperidino, hexamethyleneimino, morpholino, or 2,6-dimethylmorpholino which comprises oxidizing with an alkali metal hypochlorite, at a temperature between —5° C and below 30° C. an aqueous suspension of a sulphenamide of the formula:

(II)

in which R and R' have the same significance as in formula (I) in the presence of a sufficient amount of an alkaline agent selected from sodium carbonate, sodium bicarbonate, potassium carbonate, potassium bicarbonate and mixtures thereof so as to maintain the pH at 9 to 10.

2. A process according to claim 1 wherein the alkali metal hypochlorite is sodium hypochlorite.

3. A process for the preparation of 2-benzothiazolsulphinamides of the formula:

(I)

in which R and R' represent alkyl groups containing from 1 to 6 carbon atoms, or cycloalkyl groups containing from 5 to 7 carbon atoms or —NRR' is piperidino, hexamethyleneimino, morpholino, or 2,6-dimethylmorpholino which comprises oxidising with an alkali metal hypochlorite, at a temperature between —5° C and below 30° C. an aqueous suspension of a sulphenamide of the formula:

(II)

in which R and R' have the same significance as in formula (I).

4. A process according to claim 3 wherein the alkali metal hypochlorite is sodium hypochlorite.

5. A process for the preparation of 2-benzothiazolesulphinamides of the formula:

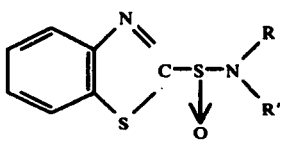 (I)

in which R and R' represent cyanoethyl groups which comprises oxidising with an alkali metal hypochlorite, at a temperature between −5° C and below 30° C. an aqueous suspension of a sulphenamide of the formula:

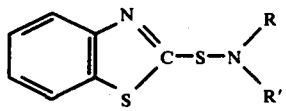

in which R and R' have the same significance as in formula (I) in the presence of a sufficient amount of an alkaline agent selected from sodium carbonate, sodium bicarbonate, potassium carbonate, potassium bicarbonate and mixtures thereof so as to maintain the pH at 9 to 10.

6. A process according to claim 5 wherein the alkali metal hypochlorite is sodium hypochlorite.

* * * * *